United States Patent [19]

Zalkin

[11] Patent Number: 4,877,023
[45] Date of Patent: Oct. 31, 1989

[54] APPARATUS FOR ARTIFICIAL VENTILATION FOR ASSISTING THE VOLUMETRIC BREATHING OF A PATIENT

[75] Inventor: Daniel Zalkin, Rambouillet, France

[73] Assignee: B.O.C.S.A., Maurepas, France

[21] Appl. No.: 160,257

[22] Filed: Feb. 25, 1988

Related U.S. Application Data

[63] Continuation-in-part of Ser. No. 799,849, Nov. 14, 1985.

[30] Foreign Application Priority Data

Nov. 20, 1984 [FR] France .................. 84 17653

[51] Int. Cl.⁴ .................................. A61M 16/00
[52] U.S. Cl. .......................... 128/204.21; 128/204.26; 128/205.15
[58] Field of Search ......... 128/204.21, 204.23–204.26, 128/205.15

[56] References Cited

FOREIGN PATENT DOCUMENTS 1237273 6/1971 United Kingdom ........... 128/205.15
2054387 6/1979 United Kingdom .

*Primary Examiner*—Max Hindenburg
*Assistant Examiner*—Randy Citrin
*Attorney, Agent, or Firm*—McAulay Fisher Nissen & Goldberg

[57] ABSTRACT

An apparatus for artificial ventilation for assisting the volumetric breathing of a patient having a demand valve connected between a source of supply of gas and a spontaneous breath tube. This demand valve comprises a reference chamber connected to an expiration tube and a user and to the output of a Venturi tube connected by its inlet to the source of supply of gas. A generator of increasing pressure is provided for transfer of a complementary flow of gas, this generator being connected by its inlet to the source of gas supply and opening out in the upstream end of the Venturi tube assisting the user's exhalation.

17 Claims, 2 Drawing Sheets

APPARATUS FOR ARTIFICIAL VENTILATION FOR ASSISTING THE VOLUMETRIC BREATHING OF A PATIENT

BACKGROUND OF THE INVENTION

This application is a continuation-in-part of application Ser. No. 06/799,849, filed on Nov. 14, 1985.

The present invention relates to a process and an apparatus for artificial ventilation for assisting the volumetric inspiration of a patient.

Modern respirators such as, for example, the one described in United Kingdom patent No. 2,054,387, employ modes of ventilation in which a patient breathes intermittently or continuously in a spontaneous manner. With such apparatus, when the patient inspires spontaneously in the circuit of the apparatus, a device detects the drop in pressure appearing at the beginning of inspiration, or "suction", and provokes a rise in pressure of the circuit to a level higher by some millibars than the initial level. This aids in the transfer of the gas insufflated towards the lungs. This level of pressure is predetermined by the prescriber or prescribing physician of the ventilation. When the patient has received a volume of gas such that the rise in the intrapulmonary pressure is equal to the rise in the pressure of the circuit, the resistance that the patient then opposes against the flow rate of gas interrupts the phase of inspiration. By control of the low rate, the patient is thus ensured a flow rate of inspiration gas corresponding to a balanced pressure or positive end of expiration pressure, hereinafter designated "PEEP", by detecting the drop in pressure of the flow of gas towards the patient caused by the inspiration and by increasing the flow rate of this gas flow proportionally to the drop in pressure detected with respect to balanced pressure PEEP.

The apparatus carrying out such a process comprises a source of supply of pressurized gas, an inspiration tube connected to the patient, a demand valve connected between the source of supply and the inspiration tube. The demand valve which constitutes means for controlling the flow rate of gas distributed towards the patient as it comprises a reference chamber connected to an expiration tube connected to the patient and to the output of a Venturi tube communicating by its inlet to a supply tube connecting it to the source of supply of gas in order to control the demand valve so that it sends the gas to the patient at the balanced pressure or positive end of expiration pressure PEEP.

The interest of such a process is obvious for a patient whose breathing is insufficient, since it is demonstrated that, from the hemodynamic standpoint, a predetermined spontaneous ventilation is preferable to a controlled ventilation in intermittent positive pressure, because the intrapulmonary pressure obtained in the first case is notably lower than in the second. However, this technique presents a considerable drawback, namely that aided inspiration induces comfort in the patient who is then not incited to make an effort. Such a situation consequently renders withdrawal difficult and leads to the necessity of making frequent adjustments of the threshold of assistance pressure.

Another patent, United Kingdom patent No. 1,237,273, owned by Blease Medical Equipment Limited, the inventor of which is Roger Edward Wentworth Manley, was brought to the inventor's attention, which shows a single air source and a bellows. However, the bellows is not used in the inhalation circuit.

OBJECTS AND SUMMARY OF THE INVENTION

It is an object of the present invention to overcome these drawbacks by a process wherein a second flow rate control ensures the transfer towards the patient of a complementary flow of gas to attain a threshold, predetermined by the prescriber of assisted respiration, of a minimum flow volume of gas effectively inspired. This flow corresponds to the integration of the flow rate during a period of inspiration; this transfer being interrupted when the predetermined threshold value is attained.

A feature of the invention is the use of a bellows in the exhalation valve.

SUMMARY OF THE INVENTION

The apparatus for carrying out the process according to the invention comprises a generator for increasing pressure to transfer a complementary flow of gas; the generator is connected by its inlet to the source of gas supply and opens out in the upstream end of the Venturi tube.

This invention also provides for a device for assisting volumetric inspiration of a particularly simple design which offers necessary and sufficient assistance for obtaining spontaneous flow volumes equal to or greater than a threshold predetermined by the prescriber. The apparatus is designed so that the patient interrupts the breathing cycle if necessary, but without provoking considerable variations in pressure in the artificial assisted ventilation circuit.

BRIEF DESCRIPTION OF THE DRAWINGS

The invention will be more readily understood on reading the following description with reference to the accompanying drawings, in which.

DESCRIPTION OF THE PREFERRED EMBODIMENTS

Figure 1:
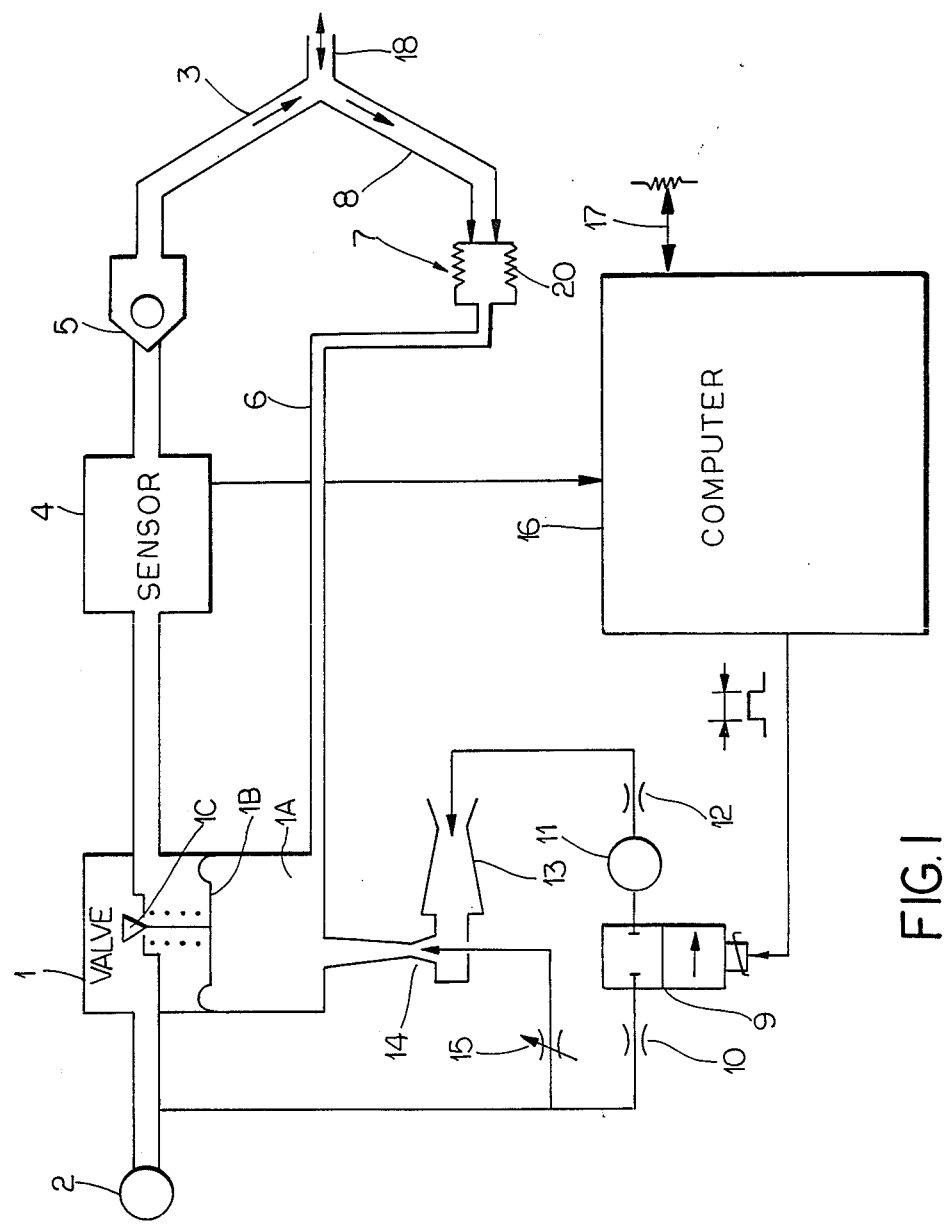
FIG. 1 is a block diagram of an artificial ventilation apparatus provided with a device for assisting volumetric inspiration according to the invention.

Referring now to the drawings, the artificial ventilation apparatus according to the invention shown in FIG. 1 comprises a demand valve 1 for use in assisting the spontaneous breathing of a patient supplied with breathable gas under pressure from a gas source 2. Such a demand valve is well known per se and is, in fact, a gas flow generator whose first control system detects a drop in pressure with respect to a balanced pressure PEEP (positive end of expiration pressure), for example, due to the inspiration of the patient. The output flow of the system is proportional to this drop in pressure. The outlet of this demand valve 1 communicates with an inspiration tube 3, connected to a patient via tube 18 which tube 18 is connected to a patient needing assisted inspiration, via an inspiration flow rate sensor 4 and a non-return valve 5. The demand valve 1 furthermore comprises a reference chamber 1A which is connected, by a conduit 6 to the interior of a bellows of an exhalation valve 7, which valve 7 is connected to an exhalation tube 8 connected to patient tube 18 for the patient. This circuit constitutes a first control of the demand valve 1, proportional to the drop in pressure in the circuit with respect to the balanced pressure PEEP. The valve of this pressure PEEP is adjustable by means which will be described hereinafter.

Demand valve 1 is a pressure controlled pressure regulator. In demand valve 1, a flexible membrane 1B separates reference chamber 1A from a valve 1C which forms demand valve 1.

According to the invention, demand valve 1 also comprises a second flow rate control which is constituted by a system for increasing pressure in the tube 3 with respect to the balanced pressure PEEP mentioned hereinbefore. The second pressure control is constituted by an increasing pressure generator 9-13 comprising an electro-valve 9 connected to the source of gas supply 2, via a first throttle 10, and to the reference chamber 1A of the control valve 1 via a capacitor 11, a second throttle 12 and a second Venturi tube 13 having an inlet opened to ambient air. This second Venturi tube 13 itself opens out in the upstream end of a first Venturi tube 14 producing the balanced pressure PEEP. Variable throttle 15 is connected with gas supply 2 and Venturi tube 14. The value of this balanced pressure PEEP may be adjusted by means of the variable throttle 15 which is connected to a supply pipe of the Venturi tube 14.

With respect to the increasing pressure generator, this is effective to transfer a complementary flow of gas to increase the flow rate imposed on the patient, the generator having an inlet connected to the source of gas supply and an outlet opening out in the upstream end of the Venturi tube 14. It should be noted that a first Venturi tube 14 has an inlet connected to the gas source 2 and an outlet in communication with a reference chamber 1a. The reference chamber 1a communicates in turn with a bellows 7 which is connected to an exhalation tube 8; gas from the gas source 2 creates a pressure in the reference chamber 1A which corresponds to PEEP pressure in the exhalation tube 8, which PEEP pressure is communicated to demand valve 1 to the patient at PEEP pressure.

The Venturi tube is known to be an air entrainement device and when no back pressure is applied to the outlet, the amount of gas entrained at the inlet of the Venturi tube depends upon the rate of driving flow and pressure of the source gas. The output flow reduces if the back pressure is increased and will eventually settle at a predetermined level that also depends on the geometry of the Venturi tube, after which the source gas flow vents through what is normally the air-intake.

When used at pressure differences (air intake to back pressure) which are close to atmospheric pressure, the maximum pressure delivered by two Venturi tubes in series is the algebraic sum of each individual maximal pressure. This provides a means of controlling independently two pressures. In this application, one Venturi tube produces the PEEP reference level and the second produces the variation during the assistance. Driving one single Venturi tube with two variable throttles would not yield an equivalent result since there is no linear relationship between the total resulting driving flow and the back pressure generated by the Venturi used in blocked output condition. In that case, the PEEP and assistance levels would become interdependent and render the control much more complex.

It makes no difference whether the Venturi tubes are at right angles or in alignment.

The inlet of Venturi tube 13 is opened to ambient air. The control flow, affected by reservoir 13 and restrictor 12, will entrain ambient air and generate a reference pressure change in chamber 1A.

Reference chamber 1A is connected through conduit 6 to a bellows unit 20 of exhalation valve 7 and through exhalation valve 7 to exhalation tube 8 leading to the patient through patient tube 18. And, reference chamber 1A also receives air from air source 2 through Venturi tube 14 and through throttle valve 15 connected between air source 2 and Venturi tube 14.

The electro-valve 9 is connected to a computer 16 which communicates with the inspiration flow rate sensor 4 and a member 17, such as a potentiometer, for adjusting the minimum spontaneous flow volume received by the patient through the inspiration tube 3. In increasing pressure generating system 9-13, electro-valve 9 is controlled by comparator 16 and responds to a signal obtained from sensor 4.

With the apparatus according to the invention, the patient first requests from the first control of the demand valve 1 the flow rate necessary for reconstituting the pressure PEEP and then the second control, i.e., the assistance device provided according to the invention, constituting the pressure increase control, in order to complete, by a complementary flow, the transfer of a gas flow rate necessary for obtaining the volume predetermined by the prescriber of assisted respiration to constitute a minimum flow volume threshold of the gas sent to the patient. The computer 16 then calculates in real time the volume to be delivered, and it controls the operation of assisted inspiration particularly by the second control. The potentiometer 17 sets in the computer 16 the minimum flow volume threshold. The increasing pressure generator constituted by the assembly of members 9-13 of the increasing pressure generator creates, on order of computer 16, a progressive increase in pressure, with respect to the balanced pressure PEEP, applied in the reference chamber 1A of the demand valve 1 in order to effect the effective flow rate for inspiration sent to the patient.

OPERATION

Figure 2:
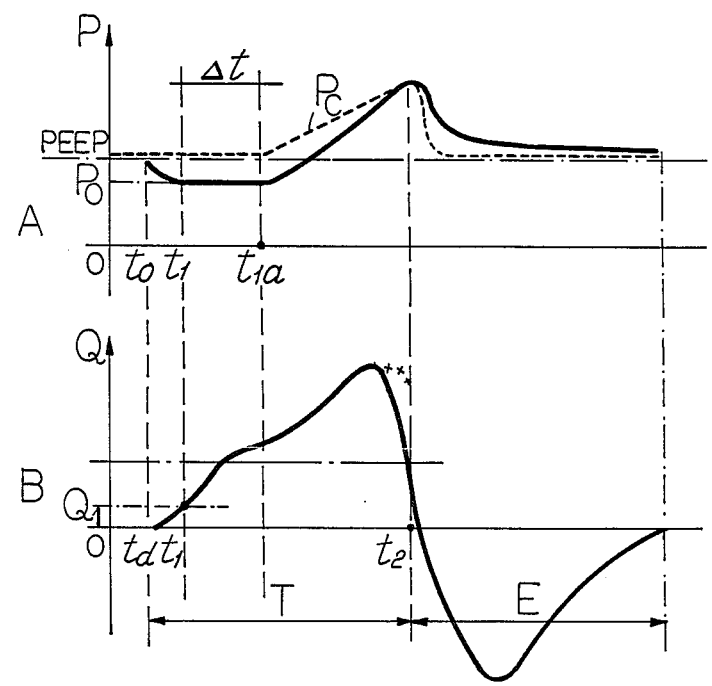
FIG. 2 is a diagram illustrating the variation in the pressure and flow rate in the course of the phases of inspiration and expiration of a complete breathing cycle as a function of time.

Referring now more particularly to FIG. 2, in connection with which the detailed operation of the apparatus which has just been described is explained.

The inspiration portion of the cycle is T and the exhalation portion of the cycle is E. Cycle portion T goes from time $t_0$ to $t_2$, and cycle portion E goes from $t_2$ to a recommencement of the inspiration cycle T at $t_0$ and completes the inspiration-exhalation cycle.

At the beginning of an inspiration cycle T (of graph A, the upper diagram of FIG. 2), the patient provokes, at instant $t_0$ corresponding to the beginning of inspiration, a suction in circuits 3, 4, 5 for connection to the demand valve 1, which suction is translated by a drop in pressure P (graph A at the top of the figure) with respect to the balanced pressure PEEP. This drop in pressure, up to value Po between time $t_0$ and $t_1$, controls the opening of the demand valve 1 which then allows a flow rate Q (graph B at the bottom of the figure) increasing from 0 at instant $t_0$, to pass towards the patient. The detection of this flow rate by sensor 4 initiates the inspiration cycle for computer 16. The computer 16 then gives the order to the pressure generator 9-13 to actuate the second progressive cycle of the demand valve 1, tending progressively to increase the flow rate imposed on the patient. This order is translated by the opening of the electro-valve 9. The second assisting Venturi tube 13 is then supplied through this electro-valve 9, throttle 10, capacitor 11 and throttle 12.

The opening of the valve 9, which is the beginning of the assisted respiration, takes place at instant $t_1$ when detection takes place of the sending towards the patient of an inspiration flow rate $Q_1$ corresponding to the threshold of opening of the assisting device (9-13).

Furthermore, in real time, the computer 16 integrates the flow rate Q going to the patient, and this is measured by the sensor 4. When the volume resulting from this integration attains the value of the predetermined threshold, which is adjusted by means of the member or potentiometer 17 for adjusting the minimum spontaneous flow volume, the computer 16 cancels the order to energize the electro-valve 9, so as to provoke closure thereof. This interrupts the control of the pressure generator (9-13) at instant $t_2$. Consequently, the second control of the demand valve 1 is cancelled, which brings about elimination of the assisted inspiration and the lowering of the pressure in the circuit 1-4-5-3 towards the value PEEP.

A maximum time of application of the assisted breathing, i.e., of the second control of the demand valve 1, is defined by the computer 16 as a function of the minimum current volume threshold predetermined by the prescriber, i.e., of the adjustment of member 17, taking into account the flow rates admissible by the patient and the result obtained during the first breathing, inspiration-exhalation cycle.

After expiration by the patient (phase E, the exhalation portion of the cycle), a new breathing cycle T-E begins and a new inspiration is effected (phase T of the cycle). During this second cycle, the computer 16 intervenes to delay the application of assisted breathing. This delay $\Delta t$ corresponds to a fraction of the assistance time calculated from the instant $t_1$ at the beginning of assistance. As may be seen in FIG. 2, the control pressure Po of the demand valve 1 indicated by the curve in broken lines in graph A of FIG. 2, begins to increase from an instant $t_{1a}$ offset by a time gap $\Delta t$ with respect to instant $t_1$. Consequently, the operation of the pressure generator 9-13, i.e., the opening of the electro-valve 9, is delayed by the time gap $\Delta t$ with respect to the instant $t_1$ of detection of inspiration. At the end of the second breathing cycle T+E, the computer 16 verifies that the volume inspired by the patient is still equal to or greater than the threshold predetermined by the adjusting member 17. In that case, during the third breathing cycle, the application of the assisted breathing, i.e., the operation of the pressure generator 914 13, is delayed by a value $\Delta t'$ which is greater than the delay $\Delta t$ introduced during the preceding second cycle. In the contrary case, if the volume inspired is less than the predetermined threshold, the delay $\Delta t$ is then decreased in the course of the third cycle. In this way, from cycle to cycle, the delay is modified until the value $\Delta t$ is attained which ensures the minimum assisted inspiration enabling the insufflation of the predetermined current volume to be obtained.

While there has been shown what is considered to be the preferred embodiments of the invention, it will be obvious to those skilled in the art that various modifications and changes may be made therein without departing from the scope of the invention.

What is claimed is:

1. Apparatus for assisting the spontaneous breathing of a patient, comprising:
    a single source of breathable gas under pressure;
    an inspiration tube and an exhalation tube, both of said tubes being connected to a patient;
    a demand valve connected between said source and said inspiration tube;
    flow rate control generator means coupled to said source;
    computer means, and sensor means connected to said computer means for detecting the flow rate of gas delivered to the patient, and wherein said computer means, in real time, calculates the volume of gas delivered to the patient and controls said generator means;
    a flow rate sensor connected to said demand valve and to said inspiration tube;
    a Venturi tube having an inlet communicating with said source and an outlet communicating with said reference chamber;
    a bellows communicating with the interior said said reference chamber and with said exhalation tube;
    means permitting breathable gas from said source to enter into said reference chamber via said Venturi tube for creating a pressure in said reference chamber which communicates simultaneously with said bellows as a PEEP pressure and with said demand valve to control the flow rate of breathable gas from said source, through said demand valve toward said inspiration tube; and
    said flow rate control generator means coupled to said source, also being coupled to said computer means and to said Venturi tube for increasing the pressure in the reference chamber in response to a demand from said flow rate sensor and thereby the flow rate of breathable gas from said source to said inspiration tube, said flow rate control generator means having an inlet connected to said single source and an outlet communicating with the inlet of said Venturi tube.

2. Apparatus according to claim 1, wherein said flow rate control generator means includes a second Venturi tube having a downstream end connected to the upstream end of said first-mentioned Venturi tube and having an upstream end connected with an electro-valve, said electrovalve being connected between said source of gas via a first throttle, and said second Venturi tube via a capacitor and a second throttle.

3. Apparatus according to claim 2, including potentiometer means coupled with said computer means for determining the threshold of the minimum current volume of gas decided by the physician prescribing assisted respiration.

4. Apparatus according to claim 2, including potentiometer means connected with said computer means for adjusting the minimum spontaneous current volume received by the patient.

5. Apparatus according to claim 1, including potentiometer means coupled with said computer means for determining the threshold of the minimum current volume of gas decided by the physician prescribing assisted respiration.

6. Apparatus according to claim 5, wherein said potentiometer means includes means connected with said computer means for adjusting the minimum spontaneous current volume received by the patient.

7. Apparatus according to claim 1, including potentiometer means connected with said computer means for adjusting the minimum spontaneous current volume received by the patient.

8. Apparatus for assisting aspiration by a user, comprising in circuit:
 a source of supply of pressurized gas;
 demand valve means having an inlet for receiving said gas from said source and serving as a gas flow generator, said demand valve having an outlet and a reference chamber;
 flow rate sensor means responsive to a pressure drop for controlling said generator by opening said demand valve so that the outflow rate of said demand valve is in proportion to the pressure drop in the circuit relative to a balanced pressure;
 a breathing tube for a user needing respiratory assistance connected to said flow rate sensor means;
 first flow rate control means for said demand valve, including a one-way non-return valve between said sensor and said breathing tube, and an exhalation tube for the user connected to an exhalation valve containing an bellows, the interior of said bellows being connected with said reference chamber;
 second flow rate control means comprising an electrovalve connected to said source of supply and an increasing pressure generator, and a throttle between said second flow rate control means and said chamber of said demand valve;
 a first Venturi tube having an inlet and an outlet, said outlet being connected to said chamber of said demand valve;
 a second Venturi tube forming part of said second flow rate control means, said second Venturi tube having one end opening out into the upstream end of said first Venturi tube such that gas flowing through said second Venturi tube issues into said first Venturi tube to produce said balanced pressure;
 means including a variable throttle for adjusting said balanced pressure and connecting said inlet of said first Venturi tube to said source of supply of pressure gas; and
 computer means connected to said electrovalve and to said flow rate sensor means for energizing and de-energizing said electrovalve, said flow rate sensor means sending to said computer a signal corresponding to the volume of gas delivered to the user whereupon said computer means calculates in real time the volume of gas to be delivered, said computer means integrating said flow rate to cancel assisted breathing by closing said electrovalve and interrupting control of said gas flow generator.

9. The apparatus according to claim 1, including potentiometer means connected with said computer means for adjusting the minimum spontaneous current volume of gas delivered.

10. The apparatus as claimed in claim 1, wherein said reference chamber communicates with said bellows in said demand valve means, said reference chamber also being in communication with said exhalation tube, and gas from said gas source applied to said demand valve creates a pressure in the reference chamber corresponding to a PEEP pressure in said exhalation tube, said PEEP pressure being communicated to said demand valve means thereby to permit the flow of gas from said gas source through said demand valve means to the user.

11. Apparatus as claimed in claim 10, wherein said first flow rate control means includes means which in response to the opening of said demand valve controls said flow rate sensor means.

12. The apparatus according to claim 11, including potentiometer means connected with said computer means for adjusting the minimum spontaneous current volume of gas delivered.

13. The apparatus according to claim 10, including potentiometer means connected with said computer means for adjusting the minimum spontaneous current volume of gas delivered.

14. The apparatus according to claim 1, including potentiometer means connected with said computer means for adjusting the minimum spontaneous current volume of gas delivered.

15. An apparatus including a demand valve for assisting spontaneous breathing, having a source of supply of pressurized gas, a breathing tube, said breathing tube being adapted for connection to a patient, and said demand valve being connected between the source of supply and said breathing tube, said demand valve constituting means for controlling the flow rate of gas distributed towards the patient, and said apparatus further comprising:
 a bellows, a first Venturi tube having an inlet connected to said source of supply of pressurized gas and an outlet, and a reference chamber in said demand valve connected to an exhalation tube through said bellows and to said outlet of said first Venturi tube connected to said source of supply of gas for control of said demand valve and to cause it to flow gas to the patient at the balanced pressure or positive end of exhalation pressure "PEEP";
 increasing pressure generator means comprising a second Venturi tube having a downstream end connected to the upstream end of said first Venturi tube and having an upstream end connected with an electrovalve, said electrovalve being connected between said source of supply via a first throttle, and said second Venturi tube via a capacitor and a second throttle,
 said increasing pressure generator means transferring a complementary flow of gas to increase the flow rate imposed on the patient, said generator means having an inlet connected to said source of gas supply and an outlet opening out in the upstream end of said second Venturi tube;
 computer means having an output connected to said electrovalve, and a sensor connected to said demand valve detecting the flow rate of gas delivered to the patient, said sensor being connected to said computer, said computer means being connected with said increasing pressure generator, and wherein said computer means, in real time, calculates the volume of gas delivered to the patient and controls said increasing pressure generator and in particular said electrovalve.

16. The apparatus according to claim 15 including potentiometer means coupled with said computer means for determining the threshold of the minimum current volume of gas decided by the physician prescribing assisted respiration.

17. The apparatus according to claim 15, including potentiometer means connected with said computer means for adjusting the minimum spontaneous current volume received by the patient.

* * * * *